(12) United States Patent
Kilgour et al.

(10) Patent No.: US 6,444,745 B1
(45) Date of Patent: Sep. 3, 2002

(54) SILICONE POLYMER NETWORK COMPOSITIONS

(75) Inventors: John A. Kilgour; Michael J. O'Brien, both of Clifton Park; Atchara Chaiyawat, Ballston Lake, all of NY (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/592,193

(22) Filed: Jun. 12, 2000

(51) Int. Cl.$^7$ ................................................ C08L 83/12
(52) U.S. Cl. ...................... 524/588; 524/612; 524/858; 524/860; 524/863; 528/408; 528/418; 424/486
(58) Field of Search ................................ 524/588, 612, 524/858, 860, 863; 528/408, 418; 424/486

(56) References Cited

U.S. PATENT DOCUMENTS

| | | | |
|---|---|---|---|
| 4,279,717 A | | 7/1981 | Eckberg et al. |
| 4,959,404 A | * | 9/1990 | Nakane et al. |
| 4,970,252 A | | 11/1990 | Sakuta et al. |
| 4,980,167 A | | 12/1990 | Harashima et al. |
| 4,987,169 A | | 1/1991 | Kuwata et al. |
| 5,128,431 A | | 7/1992 | Riding et al. |
| 5,236,986 A | | 8/1993 | Sakuta |
| 5,266,321 A | | 11/1993 | Shukuzaki et al. |
| 5,354,796 A | | 10/1994 | Creecy et al. |
| 5,412,004 A | | 5/1995 | Tachibana et al. |
| 5,493,041 A | | 2/1996 | Biggs et al. |
| 5,567,428 A | * | 10/1996 | Hughes |
| 5,599,533 A | | 2/1997 | Stepniewski et al. |
| 5,654,362 A | | 8/1997 | Schulz, Jr. et al. |
| 5,663,752 A | | 9/1997 | Imamura et al. |
| 5,703,041 A | | 12/1997 | Afriat et al. |
| 5,760,116 A | | 6/1998 | Kilgour et al. |
| 5,811,487 A | | 9/1998 | Schulz, Jr. et al. |
| 5,833,973 A | | 11/1998 | Dobkowski et al. |
| 5,854,336 A | | 12/1998 | Divone, Sr. et al. |
| 5,880,210 A | | 3/1999 | Schulz, Jr. et al. |
| 5,889,108 A | | 3/1999 | Zhang |
| 5,919,437 A | | 7/1999 | Lee et al. |
| 5,922,308 A | | 7/1999 | Brewster et al. |
| 5,922,309 A | | 7/1999 | Brewster |
| 5,928,660 A | | 7/1999 | Kobayashi et al. |
| 5,961,961 A | | 10/1999 | Dobkowski et al. |
| 6,039,935 A | | 3/2000 | Mohammadi |
| 6,042,815 A | | 3/2000 | Kellner et al. |
| 6,074,672 A | | 6/2000 | Dobkowski et al. |

FOREIGN PATENT DOCUMENTS

| | | |
|---|---|---|
| EP | 0 420 253 A | 4/1991 |
| EP | 0 545 002 A | 6/1993 |
| EP | 0 790 055 A1 | 8/1997 |
| EP | 1 112 733 A | 7/2001 |
| GB | 2 129 820 A | 5/1984 |
| JP | 61194009 | 8/1986 |
| JP | 01190757 | 7/1989 |
| JP | 01207354 | 8/1989 |
| JP | 01250305 | 10/1989 |
| JP | 02172906 | 7/1990 |
| JP | 03197413 | 8/1991 |
| WO | WO 97/44010 | 11/1997 |
| WO | WO 98/00097 | 1/1998 |
| WO | WO 98/00098 | 1/1998 |
| WO | WO 98/00102 | 1/1998 |
| WO | WO 98/00103 | 1/1998 |
| WO | WO 98/00105 | 1/1998 |
| WO | WO 98/04236 | 2/1998 |
| WO | WO 98/18438 | 5/1998 |
| WO | WO 98/18849 | 5/1998 |
| WO | 0 882 753 A | 12/1998 |
| WO | WO 98/42307 | 12/1998 |
| WO | WO 99/51192 | 10/1999 |
| WO | WO 00/08087 | 2/2000 |
| WO | 1 057 872 A | 12/2000 |
| WO | WO 01/14458 A | 3/2001 |

OTHER PUBLICATIONS

Mei H.L., et. al. "Ionic Conductive Polymers Based on Polymethylsiloxane Graft–Cross Linked with Oligo (ethylene oxide)" Polymers for Advanced Technologies, GB, John Wiley and Sons, Chichester, vol. 1, No. 3/04, Jun. 1, 1990, pp. 239–245 XP 000311611 ISSN: 1042–7147.

J.V. Crivello and N. Fan, J. Polymer Sci., Part A: *Polymer Chemistry*, pp. 1853–1863 (1997).

\* cited by examiner

*Primary Examiner*—Robert Dawson
*Assistant Examiner*—Kuo-Liang Peng
(74) *Attorney, Agent, or Firm*—Kenneth S. Wheelock

(57) ABSTRACT

A silicone composition containing a polyethersiloxane block copolymer network and a fluid within the network is useful as a component of various personal care compositions.

7 Claims, No Drawings

SILICONE POLYMER NETWORK COMPOSITIONS

FIELD OF THE INVENTION

The present invention relates to silicone compositions, more particularly to compositions comprising a silicone polymer network.

BRIEF DESCRIPTION OF THE RELATED ART

The personal care industry thrives on being able to deliver multiple performance products based on mixture of several components, with each having performance characteristics important to or desirable in the final formulation. One desirable characteristic is the ability to provide a silky initial feel derived from low molecular weight silicones, such as for example, octamethylcyclotetrasilioxane or decamethylcyclopentasiloxane, in the formulation while maintaining a high, but shear-thinnable viscosity. While these low molecular weight silicones provide the desired feel characteristics, they are also low viscosity, highly flowable liquids. Thus they are not easily held in a formulation, preferring rather to separate and flow out of a given container or flow uncontrollably across the skin when used in a specific application. Further, it desirable to achieve an initial silky feel while providing a smooth, low-residue feel upon dry-down. Polymeric silicone gels prepared in volatile silicone been found to deliver desirable initial feel of volatile, low viscosity silicones to formulations while at the same time provide high viscosity and a smooth silky feel on dry-down, see for example, U.S. Pat. Nos. 5,760,116, 5,493,041 and 4,987,169.

Such polymeric silicone gels have typically been made by the hydrosilylation reaction, which requires the use of both SiH functional groups and terminal olefinic groups to form crosslinked siloxane polymers. Thus only siloxane structures that can incorporate silylhydride groups and optionally, vinyl functional siloxane groups, can be utilized in making these materials. Further this method of generating crosslinked siloxane polymers limits the range of desirable organofunctional groups that may be incorporated into the polymeric structure to create additional performance advantages in complex formulations. Thus attempts to include organofunctional groups into the crosslinked siloxane polymer include unsaturated organic groups compatible with the hydrosilylaton reaction.

SUMMARY OF THE INVENTION

In a first aspect, the present invention relates to a silicone composition, comprising:

(a) a polyethersiloxane block copolymer network, comprising:

one or more polyether blocks, each comprising two or more structural units of the formula (I):

$$—R^1O— \qquad (I)$$

wherein each $R^1$ is independently a divalent hydrocarbon radical or $R^2$, wherein $R^2$ is a trivalent hydrocarbon radical, and one or more polysiloxane blocks, each comprising two or more structural units of the formula (II):

$$—R^3{}_2SiO_{2/2}— \qquad (II)$$

wherein each $R^3$ is independently a monovalent hydrocarbon radical or $R^2$, and wherein at least one polyether block of the copolymer network is bonded to at least one polysiloxane block of the copolymer network by a link according to formula (III):

wherein the $R^2O$ unit of the structure of formula (III) is a unit of the at least one polyether block and the $R^2R^3SiO_{2/2}$ unit of the structure of formula (III) is a unit of the at least one polysiloxane unit, and (b) a fluid within the network.

In a second aspect, the present invention is directed to a method for making a silicone composition, comprising polymerizing an epoxy functional organosiloxane compound in the presence of an acid catalyst and a fluid.

In a third aspect, the present invention is directed to a personal care composition comprising the polyethersiloxane block copolymer network of the present invention.

In a fourth aspect, the present invention is directed to a method for making a personal care composition, comprising combining one or more personal care ingredients with a polyethersiloxane block copolymer network of the present invention.

In a fifth aspect, the present invention is directed to a method for reversibly imparting characteristics of a solid to a fluid, comprising introducing the fluid into a polyethersiloxane block copolymer network of the present invention.

The copolymer network of the present invention exhibits, in its various embodiments, a high affinity for a wide variety of fluids, including emollient fluids. The silicone composition of the present invention exhibits good stability, that is a high resistance to separation of the fluid from the silicone composition. Personal care compositions containing the copolymer network and an emollient fluid, whether the copolymer network and fluid are added separately to the personal care composition or added to the personal care composition in the form of the silicone composition of the present invention, exhibit improved sensory feel, leave a smooth silky feeling in the skin upon dry down and exhibit good stability, that is, a high resistance to separation of the emollient fluid from the personal composition.

DETAILED DESCRIPTION OF THE INVENTION

As used here in, the terminology "network" means a three dimensionally extending structure comprising interconnected polyethersiloxane block copolymer chains. Preferably, fluid is contained within interstices of the network. The term "interstices" is used herein in reference to a network to denote sp aces within the network, that is, spaces between the polyethersiloxane block copolymer chains of the network.

In a preferred embodiment, the polyethersiloxane block copolymer network is a crosslinked network that is insoluble in the fluid component of the silicone composition of the present invention, but that is capable of being swollen by the fluid. The amount of crosslinking present in the crosslinked network may be characterized with respect to the degree of swelling exhibited by the network in the fluid. In a preferred embodiment, the crosslinked structure of the network is effective to allow the network to be swollen by a molecular weight silicone fluid, such as, for example, decamethylcyclopentasiloxane, from its original volume to a swollen volume that is a factor of from 1.01 to 5000, more preferably from 2 to 1000, and even more preferably from 5 to 500, times its original volume. The original volume of the network can be determined, for example, by extracting or evaporating all of the fluid component for the silicone composition of the present invention to leave the original volume, that is, the volume of the polyethersiloxane block copolymer network in the absence of the fluid.

As used herein the terminology "hydrocarbon radical" includes acyclic hydrocarbon radicals, alicyclic hydrocarbon radicals and aromatic hydrocarbon radicals.

As used herein in reference to a hydrocarbon radical, the term "monovalent" means that the radical is capable of forming one covalent bond per radical, the term "divalent" means that the radical is capable of forming two covalent bonds per radical and the term "trivalent" means that the radical is capable of forming three covalent bonds per radical. Generally, a monovalent radical can be represented as having been derived from a saturated hydrocarbon compound by conceptual removal of one hydrogen atom from the compound, a divalent radical can be represented as having been derived from a saturated hydrocarbon compound by conceptual removal of two hydrogen atoms from the compound and a trivalent radical can be represented as having been derived from a saturated hydrocarbon compound by conceptual removal of three hydrogen atoms from the compound. For example, an ethyl radical, that is, a $CH_2CH_3$ radical, is an monovalent radical, a dimethylene radical, that is, a
$(CH_2)_2$— radical, is an a divalent radical and an ethanetriyl radical, that is, an

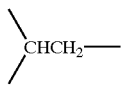

radical, is a trivalent radical, each of which can be represented as having been derived by conceptual removal of one or more hydrogen atoms from the saturated hydrocarbon ethane.

As used herein, the terminology "acyclic hydrocarbon radical" means a straight chain or branched hydrocarbon radical, preferably containing from 1 to 60 carbon atoms per radical, which may be saturated or unsaturated and which may be optionally substituted or interrupted with one or more atoms or functional groups, such as, for example, carboxyl, cyano, hydroxy, halo and oxy. Suitable monovalent acyclic hydrocarbon radicals include, for example, alkyl, alkenyl, alkynyl, hydroxyalkyl, cyanoalkyl, carboxyalkyl, alkyloxy, oxaalkyl, alkylcarbonyloxaalkylene, carboxamide and haloalkyl, such as, for example, methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl. Suitable divalent acyclic hydrocarbon radicals include, for example, linear or branched alkylene radicals, such as, for example, methylene, dimethylene, trimethylene, decamethylene, ethylethylene, 2-methyltrimethylene, 2,2-dimethyltrimethylene and linear or branched oxalkylene radicals such as, for example, methyleneoxypropylene. Suitable trivalent acyclic hydrocarbon radicals include, for example, alkanetriyl radicals, such as, for example, 1,1,2-ethanetriyl, 1,2,4-butanetriyl, 1,2,8-octanetriyl, 1,2,4-cyclohexanetriyl and oxaalkanetriyl radicals such as, for example, 1,2,6-triyl-4-oxahexane.

As used herein the term "alkyl" means a saturated straight or branched monovalent hydrocarbon radical. In a preferred embodiment, monovalent alkyl groups are selected from linear or branched alkyl groups containing from 1 to 60 carbons per group, such as, for example, methyl, ethyl, propyl, iso-propyl, n-butyl, iso-butyl, sec-butyl, tert-butyl, pentyl, hexyl, heptyl, decyl, dodecyl.

As used herein the term "alkenyl" means a straight or branched monovalent terminally unsaturated hydrocarbon radical, preferably containing from 2 to 10 carbon atoms per radical, such as, for example, ethenyl, 2-propenyl, 3-butenyl, 5-hexenyl, 7-octenyl and ethenylphenyl.

As used herein, the terminology "alicyclic hydrocarbon radical" means a radical containing one or more saturated hydrocarbon rings, preferably containing from 4 to 12 carbon atoms per ring, per radical which may optionally be substituted on one or more of the rings with one or more alkyl radicals, each preferably containing from 2 to 6 carbon atoms per alkyl radical, halo radicals or other functional groups and which, in the case of a monovalent alicyclic hydrocarbon radical containing two or more rings, may be fused rings. Suitable monovalent alicyclic hydrocarbon radicals include, for example, cyclohexyl and cyclooctyl. Suitable divalent hydrocarbon radicals include, saturated or unsaturated divalent monocyclic hydrocarbon radicals, such as, for example, 1,4-cyclohexylene. Suitable trivalent alicyclic hydrocarbon radicals include, for example, cycloalkanetriyl radicals such as, for example, 1-dimethylene-2,4-cyclohexylene, 1-methylethylene-3-methyl-3,4-cyclohexylene.

As used herein, the terminology "aromatic hydrocarbon radical" means a hydrocarbon radical containing one or more aromatic rings per radical, which may, optionally, be substituted on the aromatic rings with one or more alkyl radicals, each preferably containing from 2 to 6 carbon atoms per alkyl radical, halo radicals or other functional groups and which, in the case of a monovalent aromatic hydrocarbon radical containing two or more rings, may be fused rings. Suitable monovalent aromatic hydrocarbon radicals include, for example, phenyl, tolyl, 2,4,6-trimethylphenyl, 1,2-isopropylmethylphenyl, 1-pentalenyl, naphthyl, anthryl, as well as aralkyl radicals such as, for example, 2-phenylethyl. Suitable divalent aromatic hydrocarbon radicals include, for example, divalent monocyclic arenes such as, for example, 1,2-phenylene, 1,4-phenylene, 4-methyl-1,2-phenylene, phenylmethylene. Suitable trivalent aromatic hydrocarbon radicals include, for example, trivalent monocyclic arenes such as, for example, 1-trimethylene-3,5-phenylene.

In a preferred embodiment, each said divalent hydrocarbon radical is independently an alkylene radical according to the structural formula (IV)

$$—(R^4CH)_g— \quad (IV)$$

wherein $R^4$ is H or alkyl, preferably —$(CH_2)_hCH_3$, and each g and h is independently an integer, wherein $2 \leq g \leq 8$ and $0 \leq h \leq 60$.

In a preferred embodiment, each $R^2$ is independently a trivalent hydrocarbon radical according to formula (V) or (VI):

-continued

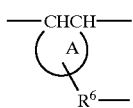
(VI)

wherein each $R^5$ and $R^6$ is independently a divalent hydrocarbon radical, and A is a saturated or unsaturated monocyclic hydrocarbon ring of, including the carbon atoms of the —CHCH— moiety set forth in formula (VI), from 5 to 12 carbon atoms, which may, optionally, be substituted on one or more carbon atoms of the ring, in addition to the carbon atom bearing the —$R^6$-moiety.

In preferred embodiment comprising $R^2$ radicals according to formula (V), one or more $R^5$ radicals are each independently alkylene or oxaalkylene. More preferably, one or more $R^5$ radicals are each independently a ($C_1$–$C_{12}$) alkylene radical or an acyclic ($C_1$–$C_{12}$)oxaalkylene radical.

In preferred embodiment comprising $R^2$ radicals according to formula (VI), one or more $R^6$ radicals are each independently linear or branched alkylene or oxaalkylene, more preferably, ($C_1$–$C_{12}$)alkylene.

In a highly preferred embodiment, one or more $R^2$ radicals are each independently hydrocarbon radicals according to the structural formula (VII), (VIII), (IX) or (X):

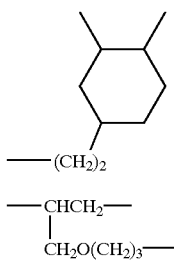
(VII)

—(CH$_2$)$_2$

—CHCH$_2$— (VIII)
|
CH$_2$O(CH$_2$)$_3$—

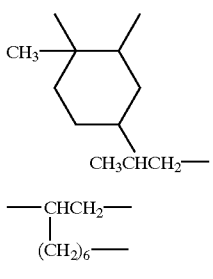
(IX)

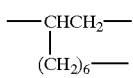
(X)

In a preferred embodiment, each $R^3$ is independently alkyl, hydroxyalkyl, a polyhydric alcohol radical, monocyclic aromatic, aralkyl, oxaalkylene or alkylcarbonyloxaalkylene. As used herein, the term "polyhydric alcohol radical" means a hydrocarbon radical containing two or more hydroxyl substituents per radical.

In a highly preferred embodiment, one or more $R^3$ radicals are each independently ($C_1$–$C_{60}$)alkyl, hydroxy ($C_1$–$C_{12}$)alkyl, polyhydric alcohol radicals according to formula (XI), (XII) or (XIII)

—$R^7$—CHOHCH$_2$OH (XI)

—$R^8$—CHOHCH$_2$CH$_2$OH (XII)

—$R^9$—C($R^{10}$)$_3$ (XIII)

wherein each $R^7$, $R^8$ and $R^9$ is independently ($C_1$–$C_{12}$) alkylene or ($C_1$–$C_{12}$)oxaalkylene and each $R^{10}$ is independently H, hydroxy, ($C_1$–$C_{12}$)alkyl, or hydroxy($C_1$–$C_{12}$)alkyl, provided that at least two $R^{10}$ substituents per radical are hydroxy or hydroxy($C_1$–$C_{12}$)alkyl, aralkyl according to the formula (XIV):

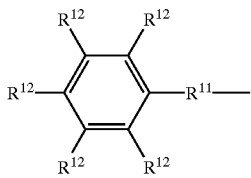
(XIV)

wherein $R^{11}$ is ($C_1$–$C_6$)alkylene and each $R^{12}$ is independently H, hydroxyl, ($C_1$–$C_6$)alkyl, hydroxy($C_1$–$C_6$)alkyl, or —OCOR$^{13}$, wherein $R^{13}$ is ($C_1$–$C_6$)alkyl, oxaalkylene according to formula (XV) or (XVI):

—(CH$_2$)$_a$O(CR$^{14}$H)$_b$— (XV)

—(CH$_2$)$_c$(O(CR$^5$H)$_d$)$_e$(CH$_2$)$_f$— (XVI)

wherein each $R^{14}$ and $R^{15}$ is independently H or alkyl, preferably ($C_1$–$C_8$)alkyl, and each a, b, c, d, e and f is independently an integer of from 1 to 20, or alkylcarbonyloxaalkylene according to formula (XVII):

—$R^{16}$—C—$R^{17}$$_3$ (XVII)

wherein $R^{16}$ is ($C_1$–$C_{12}$)alkylene or ($C_1$–$C_{12}$)oxaalkylene and each $R^{17}$ is independently H, ($C_1$–$C_{24}$)alkyl, or —OCOR$^{18}$, wherein each $R^{18}$ is independently ($C_1$–$C_{24}$) alkyl, provided that at least one $R^{17}$ group per radical is —OCOR$^{18}$.

In a highly preferred embodiment, one or more $R^3$ radicals are each independently ($C_{20}$–$C_{60}$)alkyl, hydroxy ($C_1$–$C_{12}$)alkyl, 2-phenylethyl, 2-methyl-2-phenylethyl, polyhydric alcohol radicals according to formula (XVIII) or (XIX):

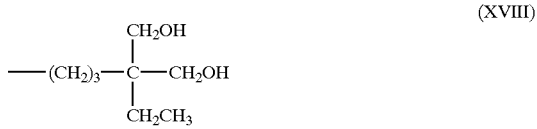
(XVIII)

—(CH2)$_4$OCHOHCH$_2$OH (XIX)

oxaalkylene according to formula (XX):

—CH$_2$O(CH$_2$CH$_2$O)$_g$(CH$_2$CH$_2$CH$_2$O)$_h$H (XX)

wherein g and h are each integers of from 0 to 50, provided that g and h cannot both be 0, or alkylcarbonyloxaalkylene according to formula (XXI):

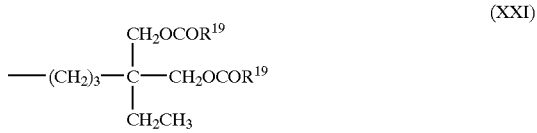
(XXI)

wherein each $R^{19}$ is independently ($C_1$–$C_{24}$)alkyl.

In a preferred embodiment, the first blocks of the polyethersiloxane block copolymer network comprise, on average, from 2 to 500, more preferably from 2 to 100, and still more preferably from 4 to 20, structural units of the formula (I) per block and the second blocks of the polyethersiloxane block copolymer network comprise, on average, from 2 to 5000, more preferably from 25 to 1000, and still more preferably from 50 to 500, structural units of the formula (II) per block.

In a preferred embodiment, the polyethersiloxane block copolymer network comprises from 0.2 to 500, more preferably from 0.4 to 250 structural units of the formula (I) per 100 structural units of formula (II).

In a preferred embodiment, from 0.1 to 10, more preferably, from 1 to 8 structural units of the formula (II) per 100 structural units according to formula (II) are each bonded to respective structural unit according to formula (I) by a link according to formula (III).

In a preferred embodiment, the polyethersiloxane block copolymer is made by a method which comprises reacting an epoxy functional organosiloxane compound comprising, per molecule of the compound, one or more, more preferably 1.5 or more and still more preferably 2 or more, structural units of the formula (XXII):

$$R^{20}{}_i SiO_{4-i/2} \quad (XXII)$$

wherein each $R^{20}$ is independently a monovalent hydrocarbon radical, provided that at least one $R^{20}$ group per unit is a monovalent epoxy-functional hydrocarbon radical and i is an integer wherein $0 \leq i \leq 3$.

In a preferred embodiment, the epoxy functional organosiloxane comprises one or more compounds according to the structural formula (XXIII):

$$Q_j T_k T^*{}_l D_m D^*{}_n M_o M^*{}_p \quad (XXIII)$$

wherein:

M is $R^{21}{}_3 SiO_{1/2}$,
M* is $R^{22}{}_2 R^{23} SiO_{1/2}$,
D is $R^{24}{}_2 SiO_{2/2}$,
D* is $R^{25} R^{26} SiO_{2/2}$,
T is $R^{27} SiO_{3/2}$,
T* is $R^{28} SiO_{3/2}$,
Q is $SiO_{4/2}$,
each $R^{21}, R^{22}, R^{24}, R^{25}$ and $R^{27}$ is independently monovalent hydrocarbon radical,
each $R^{23}, R^{26}$ and $R^{28}$ is independently a monovalent epoxy-functional hydrocarbon radical, and
j, k, l, m, n, o and p are each integers selected to provide a compound a having a viscosity of from 2 to 1,000,000 centiStokes ("cSt"), more preferably from 50 to 100,000 cSt, and, even more preferably, from 100 to 20,000 cSt and having a desired amount of monovalent monovalent epoxy-functional hydrocarbon radicals per molecule.

In a highly preferred embodiment, each $R^{21}, R^{22}, R^{24}, R^{25}$ and $R^{27}$ is independently $R^3$, as described above.

In a highly preferred embodiment, each $R^{23}, R^{26}$ or $R^{28}$ is independently an epoxy functional hydrocarbon radical according to formula (XXIV) or (XXV):

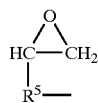

(XXIV)

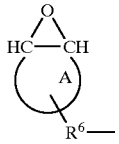

(XXV)

wherein $R^5$, $R^6$ and A are each defined as above.

Epoxy substituted siloxanes are prepared in the normal manner through the use of a hydrosilylation reaction to attach a vinyl or allyl substituted epoxide onto an SiH bearing siloxane. SiH containing siloxanes are well known in the art and can be linear, branched, or cyclic in structure. Examples of useful vinyl or allyl substituted epoxides include 4-vinyl cyclohexene oxide, allyl glycidyl ether, limonene oxide, 1,2-epoxy-5-hexene, 1,2-epoxy-7-octene, norbornadiene monoepoxide and 1,2-epoxy-9-decene. Precious metal catalysts suitable for making epoxy siloxanes are also well known in the art and include complexes of rhodium, ruthenium, palladium, osmium, iridium and platinum.

In a preferred embodiment, the epoxy functional organosiloxane compound is reacted by polymerizing the epoxy functional organosiloxane compound in the under cationic polymerization conditions and, preferably, in the presence of a fluid, preferably a volatile siloxane fluid. In one embodiment, the epoxy functional organosiloxane compound is polymerized in the presence of a fluid to directly form the silicone composition of the present invention. In another embodiment, the epoxy functional organosiloxane compound is polymerized in the presence of a first fluid or fluid mixture to form a polyethersiloxane block copolymer network, and then the network so formed is subsequently swollen with a second fluid or fluid mixture to form the silicone composition of the present invention. The second fluid or fluid mixture may be the same as or different from the first fluid mixture. The first solvent may, optionally, be removed from the polymerized network by, for example, evaporation, prior to addition of the second fluid. As a further alternative, the epoxy functional organosiloxane compound is polymerized in the absence of a fluid to form a polyethersiloxane block copolymer network and the network is subsequently swollen with a fluid or mixture of fluids to form the silicone composition of the present invention.

Cationic polymerization conditions can be generated by addition of an acid catalyst capable of polymerizing an epoxy group such as, for example, by addition of onium salt generated acids and certain metal salts, such as, for example, aluminum trichloride and ferric chloride, which act as Lewis acids or by addition of lanthanide triflates, see PCT Int. Appl. WO 0008,087. Acid catalyzed polymerization of epoxides is a well known method of forming organic polymers and has been applied to epoxy-functional siloxane compounds in order to form siloxane polyalkyleneoxide block copolymers for use in a variety of applications as, for example, release coatings on paper, see, for example, U.S. Pat. No. 4,279,717, and in conjunction with organic materials to form coatings and modified plastic compositions, see for example, U.S. Pat. Nos. 5,354,796 and 5,663,752.

In a preferred embodiment, the epoxy functional organosiloxane compound is polymerized under cationic cure conditions generated through the interaction with platinum and an SiH-containing compound. This epoxide polymerization reaction route is described in U.S. Pat. No. 5,128,431 and by J. V. Crivello and N. Fan, *J. Polymer Sci., Part A: Polymer Chemistry*, pp.1853–1863 (1997).

The method of polymer synthesis provides for incorporation of a wide range of organofunctional groups into the copolymeric structure. Thus, the inclusion of other organofunctional groups, such as, for example, organic epoxides, epoxysiloxanes, terminally unsaturated organic and alkenylsiloxane compounds can be used to modify the resulting copolymers.

In one embodiment, the organofunctional groups are introduced to the network as $R^{21}$, $R^{22}$, $R^{24}$, $R^{25}$ and $R^{27}$ radicals present on an epoxyfunctional organosiloxane according to formula (XXIII) above. In an alternative embodiment, the organofunctional groups are introduced to the network during polymerization of the epoxyfunctional organosiloxane by including organofucntional compounds to the reaction mixture which are copolymerizable with the epoxy functional organosiloxane under the chosen polymerization reaction conditions.

In one embodiment, polymerization of the epoxy functional organosiloxane is conducted in the presence of one or more organic epoxide compounds which are copolymerizable with epoxy functional siloxanes under the polymerization conditions to form mixed polyalkyleneoxide units. The additional organic epoxide compounds may contain different substituents to further modify the resulting block copolymer. Suitable organic epoxide compounds include, for example, ethylene oxide, propylene oxide, butylene oxide, cyclohexene oxide and glycidol.

In another embodiment, the polymerization of the epoxy functional organosiloxane is conducted in the presence of one or more hydroxyl functional compounds which are copolymerizable with epoxy functional siloxanes under the polymerization conditions to modify the product block copolymer. Suitable hydroxyl functional compounds include, for example, hydroxy-stopped polyethers, organic alcohols, including organic diols, carbinol functional siloxanes and hydroxy functional organopolysiloxane polymers, including polyethersiloxane copolymers.

In another embodiment, the polymerization of the epoxy functional organosiloxane is conducted in the presence one or more alkenyl functional compounds which are copolymerizable with epoxy functional siloxanes under the polymerization conditions to modify the product block copolymer. Suitable alkenyl functional compounds include alkenyl functional organic compounds, such as, for example, hexadiene, and alkenyl functional silicone compounds, such as for example, vinyl polydimethylsiloxanes. For example, an alkenyl-functional compound may conveniently be added via hydrosilylation in those embodiments in which the cationic reaction conditions for reacting the epoxide groups are generated using platinum and a hydrido-substituted siloxane, as described above.

The silicone composition may be further processed under low to high shear to adjust the viscosity and sensory feel of the composition. This may be achieved, for example, by subjecting the composition to a moderate to high shearing force. High shear may be applied using, for example, a Sonolator apparatus, a Gaulin Homogenizer or a Micro Fluidizer apparatus. Optionally, one or more fluids may be added to the silicone composition prior to the shearing.

In a preferred embodiment, the silicone composition of the present invention is a solid, typically having a creamy consistency, wherein the copolymer network acts as a means for gelling the fluid to reversibly impart characteristics of a solid to the fluid. At rest, the silicone composition exhibits the properties of a solid gel material. The silicone composition of the present invention exhibits high stability and resistance to syneresis, that is, the composition exhibits little or no tendency for fluid to flow from the composition and imparts high stability and syneresis resistance to personal care compositions which include the silicone composition as a component. The high stability and syneresis resistance persists with prolonged aging of such silicone compositions and personal care compositions. However, fluid may be released from the network by subjecting the silicone composition to a shearing force, such as, for example, by rubbing the composition between one's fingers, to provide improved sensory feel characteristic of the fluid component of the silicone material.

Fluids suitable for use as the fluid component of the composition of the present invention are those compounds or mixtures of two or more compounds that are in the liquid state at or near room temperature, for example, from about 20° C. about 50° C., and about one atmosphere pressure, and include, for example, silicone fluids, hydrocarbon fluids, esters, alcohols, fatty alcohols, glycols and organic oils. In a preferred embodiment, the fluid component of the composition of the present invention exhibits a viscosity of below about 1,000 cSt, preferably below about 500 cSt, more preferably below about 250 cSt, and most preferably below 100 cSt, at 25° C.

In a preferred embodiment, the fluid component of the present invention comprises an emollient compound. Suitable emollient compound include any fluid that provides emollient properties, that is, that when applied to skin, tend to remain on the surface of the skin or in the stratum corneum layer of the skin to act as lubricants, reduce flaking and to improve the appearance of the skin. Emollient compound are generically known and include, for example, hydrocarbons, such as for example, isododecane, isohexadecane and hydrogenated polyisobutene, organic waxes, such as for example, jojoba, silicone fluids, such as, for example, cyclopentasiloxane, dimethicone and bisphenylpropyl dimethicone, esters, such as, for example, octyldodecyl neopentanoate and oleyl oleate, as well as fatty acids and alcohols, such as for example, oleyl alcohol and isomyristyl alcohol.

In a highly preferred embodiment, the fluid component of the present invention comprises a silicone fluid, more preferably a silicone fluid that exhibits emollient properties. Suitable silicone fluids include, for example, cyclic silicones of the formula $D_r$, wherein D is defined as above, $R^{23}$ is $(C_1-C_6)$alkyl, preferably methyl, and r is an integer wherein $3 \leq r \leq 12$, such as, for example, hexamethylcyclotrisiloxane ("$D_3$"), octamethylcyclotetrasiloxane ("$D_4$"), decamethylcyclopentasiloxane ("$D_5$"), and dodecamethylcyclohexasiloxane ("$D_6$") as well as linear or branched organopolysiloxanes having the formula (XXVI):

$$M'D'_qT_rM' \qquad (XXVI)$$

wherein:

M' is $R^{29}_3SiO_{1/2}$;

D' is $R^{30}_2SiO_{2/2}$;

T' is $R^{31}SiO_{3/2}$ $R^{29}$, $R^{30}$ and $R^{31}$ are each independently alkyl, aryl or aralkyl;

q and r are each independently integers from 0 to 300, preferably from 0 to 100, more preferably from 0 to 50, and most preferably from 0 to 20.

In a preferred embodiment, the silicone composition of the present invention comprises, per 100 parts by weight ("pbw") of the silicone composition, from 0.1 to 30 pbw, more preferably from 0.5 pbw, to 20 pbw and still more preferably from 1 to 15 pbw of the polyethersiloxane block copolymer network and from 70 pbw to 99.9 pbw, more preferably from 80 pbw to 99.5 pbw, and still more preferably from 85 pbw to 99 pbw of the fluid.

Once the desired form is attained, the resulting material is generally a high viscosity cream with good feel characteristics, high absorbance of volatile siloxanes. It is capable being blended into formulations for hair care, skin care, antiperspirants, sunscreens, cosmetics, color cosmetics, insect repellants, vitamin and hormone carriers, fragrance carriers and the like.

The personal care applications where the polyethersilicone block copolymer network and the silicone composition of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, inset repellent and anti-aging products, color cosmetics such as lipsticks, foundations, face powders, eye liners, eye shadows, blushes, makeup, mascaras and other personal care formulations where silicone components have been conventionally been added, as well as drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the polyethersiloxane block copolymer network, preferably in the form of the silicone composition of the present invention. Suitable personal care compositions may be in the form of a single phase or in the form of an emulsion, including oil-in-water, water-in-oil and anhydrous emulsions, as well as multiple emulsions, such as, for example, oil-in water-in-oil emulsions and water-in-oil-in water-emulsions.

In a preferred embodiment, an antiperspirant composition comprises the polyethersiloxane block copolymer network, preferably in the form of silicone composition of the present invention, and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as, for example, aluminum-zirconium chlorohydrate, aluminum zirconium glycine complexes, such as, for example, aluminum zirconium tetrachlorohydrexgly.

In a preferred embodiment, a skin care composition comprises the polyethersiloxane block copolymer network, preferably in the form of silicone composition of the present invention, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylmethane, p-aminobenzoic acid and octyl dimethyl-p-aminobenzoic acid.

In a preferred embodiment, a color cosmetic composition, such as, for example, a lipstick, a makeup or a mascara composition comprises the polyethersiloxane block copolymer network, preferably in the form of silicone composition of the present invention, and a coloring agent, such as a pigment, a water soluble dye or a liposoluble dye.

EXAMPLE 1

The silicone gel composition of Example 1 was made as follows. 485 g of an 85:15 wt:wt blend of a first epoxy functional polyorganosiloxane containing both terminal and randomly distributed on-chain cycloaliphatic epoxy substituents, having a viscosity of 300 cSt and having an epoxy equivalent weight of 1200 grams per equivalent ("g/eq") and a second epoxy functional polyorganosiloxane containing randomly distributed on-chain cycloaliphatic epoxy substituents, having a viscosity of 740 cSt and having an epoxy equivalent weight of about 1200 g/eq, wherein each of the epoxy functional polyorganosiloxanes was made by hydrosilylation of a silylhydride functional organopolysiloxane with 4-vinyl-1-cyclohexene-1,2-epoxide ("Epoxy-functional Organopolysiloxane I") and 15 g of a trimethylsilyl-terminated methylhydrogen polysiloxane having a viscosity of about 28 cSt ("Silylhydride-functional Organopolysiloxane I") having a viscosity of about 28 cSt were dissolved in 1500 g of $D_5$. 0.1 g of a platinum divinyltetramethyldisiloxane complex (Karstedt's catalyst) was added. The mixture was heated to 80° C. for approximately 2 hours with mixing to give a fluffy gel.

EXAMPLE 2

The silicone gel composition of Example 2 was made as follows. 485 g of an epoxy functional polyorganosiloxane containing both terminal and randomly distributed on-chain cycloaliphatic epoxy substituents, having a viscosity of 300 cSt and having an epoxy equivalent weight of about 1400 g/eq, made by hydrosilylation of a silylhydride functional organopolysiloxane with 4-vinyl-1-cyclohexene-1,2-epoxide ("Epoxy-functional Organopolysiloxane II") and 15 g Silylhydride-functional Organopolysiloxane I were dissolved in 1500 g $D_5$. 0.1 g Karstedt's catalyst was added. The mixture was heated to 80° C. for approximately 2 hours with mixing to give a fluffy gel.

EXAMPLE 3

The silicone gel composition of Example 3 was made as follows. 475 g of Epoxy-functional Organopolysiloxane II, and 25 g Silylhydride-functional Organopolysiloxane I were dissolved in 1500 g of $D_5$. 0.1 g Karstedt's catalyst was added. The mixture was heated to 80° C. for approximately 2 hours with mixing to give a fluffy gel.

EXAMPLE 4

The silicone gel composition of Example 4 was made as follows. 485 g Epoxy-functional Organopolysiloxane II and 15 g Silylhydride-functional Organopolysiloxane I were dissolved in 1500 g of $D_5$. 0.1 g Karstedt's catalyst was added. The mixture was heated to 80° C. for approximately 4 hours with mixing to give a fluffy gel.

EXAMPLE 5

The silicone gel composition of Example 5 was made as follows. 475 g of an epoxy functional polyorganosiloxane containing randomly distributed on-chain cycloaliphatic epoxy substituents, having a viscosity of 460 cSt and having an epoxy equivalent weight of about 900 g/eq, made by hydrosilylation of a silylhydride functional organopolysiloxane with 4-vinyl-1-cyclohexene-1,2-epoxide ("Epoxy-functional Organopolysiloxane III") and 25 Silylhydride-functional Organopolysiloxane I were dissolved in 1500 g of $D_5$. 0.1 g Karstedt's catalyst was added. The mixture was heated to 80° C. for approximately 4 hours with mixing to give a fluffy gel.

EXAMPLE 6

The silicone gel composition of Example 6 was made as follows. 427.5 g Epoxy-functional Organopolysiloxane 11, 47.5 of diol terminated silicone polymer having a viscosity of about 800 cSt, made by hydrosilylation of silylhydride terminated organopolysiloxane with trimethylolpropane monoallyl ether, and 25 g Silylhydride-functional Organopolysiloxane I were dissolved in 1500 g of D5. 0.1 g Karstedt's catalyst was added. The mixture was heated to 80° C. for approximately 2 hours with mixing to give a fluffy gel

EXAMPLE 7

The silicone gel composition of Example 7 was made as follows. 332.5 g Epoxy-functional Organopolysiloxane II, 142.5 g of phenol substituted epoxy-functional organopolysiloxane containing randomly distributed on-chain cycloaliphatic epoxy substituents and containing 2-propyl phenol substituent groups, having a viscosity of about 265 cSt and having an epoxy equivalent weight of about 1700 g/eq, made by hydrosilylation of a silylhydride functional organopolysiloxane with 4-vinyl-1-cyclohexene-1,2-epoxide ("Epoxy-functional Organopolysiloxane IV") and 25 g Silylhydride-functional Organopolysiloxane I were dissolved in 1500 g of $D_5$. 0.1 g Karstedt's catalyst was added. The mixture was heated to 80° C. for approximately 4 hours with mixing to give a fluffy gel.

EXAMPLE 8

The silicone gel composition of Example 8 was made as follows. 412 g Epoxy-functional Organopolysiloxane II, 73 g of an epoxy terminated polydimethylsiloxane having a viscosity of about 200 cSt and having an epoxy equivalent weight of about 3800 g/eq, made by hydrosilylation of a silylhydride functional organopolysiloxane with 4-vinyl-1-cyclohexene-1,2-epoxide ("Epoxy-functional Organopolysiloxane V") and 15 g Silylhydride-functional Organopolysiloxane I were dissolved in 1500 g of $D_5$. 0.1 g Karstedt's catalyst was added. The mixture was heated to 80° C. for approximately 4 hours with mixing to give a fluffy gel.

EXAMPLE 9

The silicone gel composition of Example 9 was made as follows. 475 g Epoxy-functional Organopolysiloxane II, and 25 g trimethylsilyl terminated methylhydrogen/dimethylpolysiloxane copolymer having a silylhydride content of about 1.05 wt % H ("Silylhydride-functional Organopolysiloxane II") were dissolved in 1500 g of $D_5$. 0.1 g Karstedt's catalyst was added. The mixture was heated to 80° C. for approximately 4 hours with mixing to give a fluffy gel.

The silicone gel compositions of Examples 1–9 were compared to gage their relative ability to thicken additional $D_5$. This was done by combining the portions of each gel with $D_5$ in a 1:2 ratio and then visually comparing the viscosities of the resulting mixtures. The gels were determined to exhibit the following order from most effective to least effective in their ability to thicken additional D5:

Ex 4>>Ex 3=Ex 6>Ex 1=Ex 2=Ex 8=Ex 9>>Ex 5>Ex 7, wherein ">" means greater than, ">>" means much greater than and "=" means equal to.

EXAMPLE 11

The silicone gel composition of Example 11 was made as follows. 400 g of Epoxy-functional Organopolysiloxane II, 75 g of an vinyl terminated polydimethylsiloxane having a viscosity of about 230 cSt and 15 g Silylhydride-functional Organopolysiloxane I were dissolved in 1500 g $D_5$. 0.1 g Karstedt's catalyst was added. The mixture was heated to 80° C. for approximately 4 hours with mixing to give a fluffy gel. When mixed in a 1:2 ratio with additional $D_5$, the composition of Example 7 caused thickening somewhat better than the composition of Example 7 but not quite as well as that of Example 5.

EXAMPLE 12

The silicone gel composition of Example 12 was made as follows. 435 g of the composition of Example 3 was mixed with 565 g of additional $D_5$ and allowed to stand for 2 hours. The result was then passed through a Gaulin homogenizer at 8000 psi. The resulting material had a viscosity of 14,960 centiPoise ("cps").

EXAMPLE 13

The silicone gel composition of Example 13 was made as follows 865 g of the composition of Example 4 was mixed with 1135 g of additional D5 and allowed to stand for 2 hours. The result was then passed through a Gaulin homogenizer at 4500 psi. After one pass, the material had a viscosity of 45,500 cps. After two passes, the viscosity of the material was 24,500 cps.

EXAMPLE 14

The silicone gel composition of Example 14 was made as follows 4.50 g of the Epoxy-functional Organopolysiloxane II and 0.50 g tetramethyldisiloxane were dissolved in 15.0 g $D_5$. One drop of Karstedt's catalyst was then mixed in. The mixture was heated to 107° C. for 10 minutes, at which time the material was a hard gel.

EXAMPLE 15

The silicone gel composition of Example 15 was made as follows 5.0 g Epoxy-functional Organopolysiloxane II, 0.1 g of a 45 wt % solution of bis(dodecylphenyl)iodonium hexafluoroantimonate in a linear organic epoxide diluent, 0.1 g benzopinacole and 10 g D5 were mixed and heated to 140° C. for 10 minutes. A soft gel was obtained.

EXAMPLE 16

The silicone gel composition of Example 16 was made as follows. 50 mg of Aluminum trichloride was mixed with 4.0 g of a 10 wt % solution of a silicone poly(ethylene oxide/propylene oxide) copolymer in $D_5$ and 6.0 g of additional $D_5$. The result was placed in a 110° C. oven for a couple of minutes and mixed thoroughly. In a separate container 5.0 g Epoxy-functional Organopolysiloxane II and 5.0 g of D5 were mixed. Then the Epoxy-functional Organopolysiloxane II/$D_5$ mixture was blended into the AlCl3/silicone polyether/ $D_5$ mix. The result was heated an additional 20 minutes in the oven. At the end of this time, the material had become a moderately hard gel.

EXAMPLE 17 and COMPARATIVE EXAMPLE 1

The anhydrous clear gel antiperspirants of Example 17 and Comparative Example 1 were made by combining the listed ingredients in the relative amounts set forth below in TABLE I according to the following procedure: (1) mixed ingredients of Part A together, (2) reserving 3% of the propylene glycol for later use, the Polysorbate80 and ethanol were dissolved in PG, (3) added 30%ZAG solution in PG to product of step (2), (3) measured refractive index of Part A and Part B, and then adjusted the differences of RI using propylene glycol to increase RI of Part B or using $D_5$ to decrease RI of Part A, so that the RI of Part A and B matched within 0.0001 unit, (4) slowly added Part B to Part A under moderate mixing and (5) homogenized for 1–2 min in an Ultra Turrax T25 homogenizer.

TABLE I

| Ingredient | Ex 17 | C Ex 1 |
| --- | --- | --- |
| Part A | | |
| 40% dimethicone copolyol in D5 | 2.5 | 2.5 |
| Silicone Composition of Ex 13 | 10.25 | — |
| Cyclopentasiloxane | — | 10.25 |
| Bis-Phenylpropyl Dimethicone | 11.25 | 11.25 |
| Part B | | |
| Polysorbate 80 | 0.25 | 0.25 |
| Propylene glycol | 47.42 | 47.42 |
| 30% ZAG in PG | 23.33 | 23.33 |
| Ethanol | 5 | 5 |

The anhydrous clear gel compositions of Example 17 and Comparative Example 1 were each evaluated for sensory properties by applying the compositions on skin. Both of the compositions were translucent gels and did not provide cooling sensation when applied. The composition of Example 17 gave a softer silkier feel on the skin, compared to that of and Comparative Example 1. The compositions of Example 17 and Comparative Example 1 showed no syneresis after one week at room temperature.

EXAMPLE 18 and COMPARATIVE EXAMPLE 2

The solid antiperspirant compositions of Example 18 and Comparative Example 2 were each made by combining the listed ingredients in the relative amounts set forth below in TABLE II, according to the following procedure: (1) heating stearyl alcohol and hydrogenated castor oil to 70° C., (2) separately mixing the silicone composition of Ex 13 with $D_5$ until uniform, (3) adding the silicone mixture to the batch and mixing well, (4) adding talc, mixing and cooling the batch to 55° C. and (5) pouring the antiperspirant composition into containers. The composition of Example 18 provided a drier, powdery feel, compared the composition of comparative Example 2.

TABLE II

| Ingredient | C Ex 2 | Ex 18 |
| --- | --- | --- |
| ZAG (Reach AZP-908) | 24 | 24 |
| Silicone Composition of Ex 13 | — | 15 |
| Cyclopentasiloxane | 55 | 40 |
| Stearyl alcohol | 15 | 15 |
| Hydrogenated castor oil | 5 | 5 |
| Talc | 1 | 1 |

EXAMPLES 19–20

The soft solid antiperspirant compositions of Examples 19 and 20 were each made by combining the listed ingredients in the relative amounts set forth below in TABLE III, according to the following procedures. The composition of Example 19 was made by mixing ZAG with the silicone composition of Example 13 until uniform. The composition of Example 20 was made by premixing with the silicone composition of Example 4 with PPG-2 myristyl ether propionate and isododecane until smooth gel developed, then adding ZAG and mixing well. The compositions of Examples 19 and 20 were each creamy, soft solid antiperspirants which gave a dry feel and cushioning during rub in and showed no syneresis after one week at room temperature.

TABLE III

| Ingredient | Ex 19 | Ex 20 |
| --- | --- | --- |
| ZAG(Reach AZP-908) | 25 | 20 |
| Silicone Composition of Ex 13 | 75 | — |
| Silicone Composition of Ex 4 | — | 40 |
| PPG-2 Myristyl ether propionate | — | 20 |
| Isododecane | — | 20 |

EXAMPLE 21

The clear stick antiperspirant composition of Example 21 is made by combining the listed ingredients in the relative amounts set forth below in TABLE IV, according to the following procedure: (1) heating propylene glycol and dipropylene glycol to 100° C., (2) slowly sprinkling DBS to the mixture, (3) cooling Part A to 80° C., (4) separately, Part B is heated to 100° C. and is then added to Part A under propeller mixing, (5) the silicone composition, diisopropyl sebacate and 40% dimethicone copolyol in D5 are then added and mixed until a smooth gel formed and (6) adding Part C to the batch. and mixing until uniform.

TABLE IV

| | Relative Amount |
| --- | --- |
| Part A | |
| Dibenzylidene sorbitol | 2 |
| Propylene glycol | 31.5 |
| Dipropylene glycol | 10 |

TABLE IV-continued

| | Relative Amount |
|---|---|
| Part B | |
| 30% ZAG solution | 50 |
| Glycine | 1 |
| Part C | |
| Diisopropyl sebacate | 1 |
| | 2? |
| Silicone Composition of Ex 4 | 1.5 |
| 40% dimethicone copolyol in D5 | 2.0 |

EXAMPLE 22

The aerosol antiperspirant composition of Example 22 is made by combining the listed ingredients in the relative amounts set forth below in TABLE V, according to the following procedure: (1) mixing Part A together under a high shear homogenizer until uniform, (2) adding aluminum chlorohydrate to the batch and mixing until uniform, (3) packaging the mixture in containers and (4) charging the containers with propellant (Part C).

TABLE V

| | Relative Amount |
|---|---|
| Part A | |
| Mixture of cyclopentasiloxane, quaternium-18 hectorite and propylene carbonate (Bentone gel VS5 PC, Rheox, Hightstown, NJ) | 10 |
| Silicone Composition of Ex 13 | 8.5 |
| Cyclomethicone | 14 |
| Dimethicone 50 cst | 5 |
| Isopropyl myristate | 1.5 |
| Part B | |
| Aluminum chlorohydrate | 21 |
| Part C | |
| Isobutane | 40 |

EXAMPLE 23

The antiperspirant roll on composition of Example 23 is made by combining the listed ingredients in the relative amounts set forth below in TABLE VI, according to the following procedure: (1) mixing cyclopentasiloxane and epoxy gel under propeller mixer for 20 mins, (2) then adding Al/Zr tetrachlorohydrex Gly and mixing for 15 mins, (3) then adding silica, mixing until uniform and the batch and packaging the composition.

TABLE VI

| Ingredient | Relative Amount |
|---|---|
| Al/Zr Tetrachlorohydrex Gly | 20 |
| Cyclopentasiloxane | 66 |
| Silicone Composition of Ex 13 | 13.5 |
| Silica | 0.5 |

EXAMPLE 24

The oil-in-water lotion composition of Example 24 is made by combining the listed ingredients in the relative amounts set forth below in TABLE VII, by (1) Parts A and B are each separately made by mixing the ingredients under high shear at about 70° (2) combining Parts A and B, (3) cooling the mixture of parts A and B to about 50° C. and then (4) mixing the cooled mixture of Parts A and B with Part C.

TABLE VII

| Ingredient | Relative Amount |
|---|---|
| PART A | |
| Deionized Water | q.s. |
| Tetrasodium EDTA | 0.02 |
| Butylene Glycol | 3.00 |
| Panthenol | 0.50 |
| Mixture of henoxyethanol, Methylparaben, Ethylparaben, Propylparaben and Butylparaben | 0.80 |
| PART B | |
| Silicone Composition of Example 4 | 4.00 |
| Hydrogenated Polydecene | 8.50 |
| Glyceryl Stearate and PEC-100 Stearate | 3.00 |
| PART C | |
| Polyacrylamide, $(C_{13-14})$isoparaffin and Laureth-7 | 1.40 |
| Fragrance | 0.20 |

EXAMPLE 25

The sheer water-in-oil sunscreen lotion composition of Example 25 is made by combining the listed ingredients in the relative amounts set forth below in TABLE VIII, according to the following procedure: (1) Part A is made by combining the ingredients and heating to 65° C., (2) Part B is made by combining the ingredients, (3) Part B is then slowly added to Part A to form an emulsion and (4) after emulsion is developed, Part C is added to the batch.

TABLE VIII

| Ingredient | Relative Amount |
|---|---|
| PART A | |
| Cyclopentasiloxane/dimethicone copolyol | 0 10. |
| Butyl Methoxydibenzoylmethane | 2.0 |
| Octyl Methoxycinnamate | 7.5 |
| Octocrylene | 8.0 |
| Zinc Oxide (and) Dimethicone | 6.0 |
| Octyl Palmitate | 3.0 |
| PBG-30 Dipolyhydroxystearate | 1.5 |
| Tocopheryl Acetate | 0.5 |
| PART B | |
| NaCl | 1.5 |
| Propylene Glycol, Diazolidinyl Urea, Methylparaben and Propylparaben | 1.0 |
| Deionized Water | q.s. |
| PART C | |
| Silicone Composition of Example 13 | 7.0 |

EXAMPLE 26

The sunscreen lotion composition of Example 26 is made by combining the listed ingredients in the relative amounts set forth below in TABLE IX, according to the following procedure: (1) Part A is made by combining ingredients and heating the combined ingredients to 75° C. with moderate propeller agitation, (2) Part B is made by combining ingredients and heating to 75° C., (3) Part A is then added to Part B under high shear agitation, (4) the batch is then cooled with agitation to 45° C., (5) Part C is then added to batch as ordered with moderate propeller agitation.

TABLE IX

| Ingredient | Relative Amount |
|---|---|
| PART A | |
| Deionized Water | q.s. |
| Tetrasodium EDTA | 0.05 |
| Glycerin | 4.00 |
| Magnesium Aluminum Silicate | 0.25 |
| PART B | |
| Stearic Acid | 2.00 |
| Glyceryl Stearate SE | 1.50 |
| $C_{12-15}$ Alkyl Benzoate | 4.00 |
| Octyl Methoxycinnamate | 1.00 |
| Octyl Salicylate | 3.00 |
| Benzophenone-3 | 7.00 |
| Butylmethoxydibenzolymethane | 2.00 |
| PART C | |
| Silicone Composition of Example 13 | 7.00 |
| Phenoxyethanol, Methylparaben Ethylparaben, Butylparaben, Propylparaben | 0.25 |
| 99% TEA | 0.50 |

EXAMPLE 27

The skin treatment composition of Example 27 is made by combining the listed ingredients in the relative amounts set forth below in TABLE X and mixing until uniform.

TABLE X

| Ingredient | Relative Amount |
|---|---|
| Retinyl Palmitate | 2.0 |
| Tocopherol | 1.0 |
| Squalane | 1.0 |
| Silicone Composition of Example 13 | q.s. |

EXAMPLE 28

The foundation composition of Example 28 is made by combining the ingredients in the relative amounts set forth below in TABLE XI according to the following procedure: (1) Part A and Part B are each separately made by combining the ingredients in the relative amounts set forth in Table XI, (2) Part B is then added to Part A under moderate agitation.

TABLE XI

| Ingredient | Relative Amount |
|---|---|
| PART A | |
| Cyclopentasiloxane/dimethicone Copolyol | 12.0 |
| Dimethicone 10 cSt | 10.0 |
| Cyclopentasiloxane | 15.0 |
| Bis-Phenylpropyl Dimethicone | 10.0 |
| Silicone Composition of Example 13 | 5.0 |
| Sorbitan Sesquioleate | 1.5 |
| Polymethylsilsesquioxane (Tospearl ® 2000) | 2.0 |
| Titanium Dioxide | 8.0 |
| Iron Oxides | 2.1 |
| PART B | |
| Deionized Water | 31.2 |
| Xanthan Gum | 0.1 |
| Glycerin | 2.0 |

TABLE XI-continued

| Ingredient | Relative Amount |
|---|---|
| Magnesium Sulfate | 1.0 |
| Preservative | q.s. |
| Fragrance | q.s. |

EXAMPLE 29

The lipstick composition of Example 29 is made by combining the listed ingredients in the relative amounts set forth below in Table XII together, using roller mill, until uniform.

TABLE XII

| Ingredient | Relative Amount |
|---|---|
| Silicone Composition of Example 13 | 5.0 |
| Trimethylsiloxysilicate | 2.0 |
| Bis-Phenylpropyl Dimethicone | 40.0 |
| Isododecane | 15.1 |
| Cetearyl Methicone | 20.0 |
| Mica | 8.0 |
| Titanium dioxide | 0.8 |
| Iron oxides | 0.1 |
| D&C Red No. 7 Ca Lake | 9.0 |

EXAMPLE 30

The shampoo composition of Example 30 is made by combining the listed ingredients in the relative amounts set forth below in TABLE XIII, according to the following procedure: (1) Part A is made by combining the ingredients and heating to 65° C., (2) Part B is made by combining the ingredients and heating to 65° C., (3) Part B is then added to Part A and mixed until uniform, (4) the batch is allowed to cool to 40° C., and then NaCl is added to adjust the viscosity of composition, (5) a preservative and citric acid to adjust pH to 6–6.5 are then added. Alternatively, the silicone composition of Example 13 can also be emulsified with surfactants and water before adding to the shampoo formulation.

TABLE XIII

| Ingredient | Relative Amount |
|---|---|
| Part A | |
| Deionized water | q.s. |
| Sodium Lauryl Sulfate | 13.00 |
| Sodium Laureth Sulfate | 12.30 |
| Cocamidopropyl Betaine | 6.00 |
| Lauryl Glucoside | 4.00 |
| Part B | |
| PEG-150 Pentaerythrityl Tetrastearate | 1.50 |
| Silicone Composition of Example 13 | 2.50 |
| Part C | |
| NaCl | q.s. |
| Methylchloroisothiazolinone and Methylisothiazolinone | 0.05 |
| Citric acid | Adjust pH 6.0–6.5 |

EXAMPLE 31

The cuticle coat composition of Example 31, useful as a leave-in hair conditioner, is made by combining the listed ingredients in the relative amounts set forth below in Table XIV together until uniform. It contains the silicone composition of Example 4 as a conditioner, which also gives body to the formulation.

TABLE XIV

| Ingredient | Relative Amount |
|---|---|
| Bis-Phenylpropyl Dimethicone | 10.0 |
| Cyclopentasiloxane | 85.0 |
| Silicone Composition of Example 4 | 5.0 |

EXAMPLE 32

The rinse-off hair conditioner composition of Example 32 is made by combining the listed ingredients in the relative amounts set forth below in TABLE XV made according to the following procedure: (1) Part A is made by combining the ingredients and heating to 65° C., (2) Part B is melted in a separate container and then added to Part A, (3) the mixture then is cooled to 40° C. and the preservative is added. Alternatively, Silicone Composition of Example 13 can be emulsified with surfactants and water before adding to the conditioner.

TABLE XV

| Ingredient | Relative Amount |
|---|---|
| Part A | |
| Deionized water | q.s. |
| Hydroxyethylcellulose | 0.50 |
| Glycerin | 2.00 |
| Methylparaben | 0.20 |
| Propylparaben | 0.10 |
| Part B | |
| Behentrimonium methosulfate(and) Cetearyl alcohol | 3.00 |
| Glyceryl Stearate | 0.80 |
| Silicone Composition of Example 13 | 3.00 |
| Cetyl Alcohol | 1.50 |
| Part C | |
| Methylchloroisothiazolinone(and) Methylisothiazolinone | 0.05 |

The copolymer network of the present invention exhibits a high affinity for a wide variety of fluids, including emollient fluids. The silicone composition of the present invention exhibits good stability, that is a high resistance to separation of the fluid from the silicone composition. Personal care compositions containing the copolymer network and an emollient fluid, whether the copolymer network and fluid are added separately to the personal care composition or added to the personal care composition in the form of the silicone composition of the present invention, exhibit improved sensory feel, leave a smooth silky feeling in the skin upon dry down and good stability, that is, a high resistance to separation of the emollient fluid from the personal composition.

What is claimed is:

1. A silicone composition, comprising:

(a) a polyethersiloxane block copolymer network, comprising:

one or more polyether blocks, each comprising two or more structural units of the formula (I):

—R$^1$O—      (I)

wherein each R$^1$ is independently a divalent hydrocarbon radical or R$^2$, wherein R$^2$ is a trivalent hydrocarbon radical, and one or more polysiloxane blocks, each comprising two or more structural units of the formula (II):

—R$^3{}_2$SiO$_{2/2}$—      (II)

wherein each R$^3$ is independently a monovalent hydrocarbon radical or R$^2$, and wherein at least one polyether block of the copolymer network is bonded to at least one polysiloxane block of the copolymer network by a link according to formula (III):

 (III)

wherein the R$^2$O unit of the structure of formula (III) is a unit of the at least one polyether block and the R$^2$R$^3$SiO$_{2/2}$ unit of the structure of formula (III) is a unit of the at least one polysiloxane unit, and (b) a fluid within the network.

2. The composition of claim 1, wherein each said divalent hydrocarbon radical is independently alkylene according to the formula:

—(R$^4$CH)$_g$— wherein R$^4$ is selected from the group consisting of H, alkyl and —(CH$_2$)$_h$CH$_3$, where
each g and h is independently an integer, wherein 2≦g≦8 and 0≦h≦60.

3. The composition of claim 1, wherein each R$^2$ is independently a trivalent hydrocarbon radical according to formula (V) or (VI):

 (V)

 (VI)

wherein each R$^5$ and R$^6$ is independently a divalent hydrocarbon radical, and
A is a saturated or unsaturated monocyclic hydrocarbon ring of, including the carbon atoms of the —CHCH— moiety set forth in formula (VI), from 5 to 12 carbon atoms, which may, optionally, be substituted on one or more carbon atoms of the ring, in addition to the carbon atom bearing the —R$^6$-moiety.

4. The composition of claim 1, wherein each R$^3$ is independently alkyl, hydroxyalkyl, a polyhydric alcohol radical, monocyclic aromatic, aralkyl, oxaalkylene or alkylcarbonyloxaalkylene.

5. The composition of claim 4, wherein one or more R$^3$ substituents is each independently (C$_1$–C$_{60}$)alkyl, hydroxy (C$_1$–C$_{12}$)alkyl,
a polyhydric alcohol radical according to the formula (XI), (XII) or (XIII):

—R$^7$—CHOHCH$_2$OH      (XI)

—R$^8$—CHOHCH$_2$CH$_2$OH      (XII)

$-R^9-C(R^{10})_3$ (XIII)

wherein each $R^7$, $R^8$ and $R^9$ is independently $(C_1-C_{12})$ alkylene or $(C_1-C_{12})$oxaalkylene and each $R^{10}$ is independently H, hydroxy, $(C_1-C_{12})$alkyl, or hydroxy$(C_1-C_{12})$alkyl, provided that at least two $R^{10}$ substituents per radical are hydroxy or hydroxy$(C_1-C_{12})$alkyl, aralkyl according to the formula:

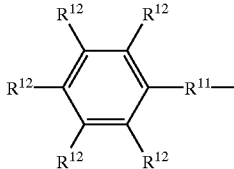

wherein $R^{11}$ is $(C_1-C_6)$alkylene and each $R^{12}$ is independently H, hydroxyl, $(C_1-C_6)$alkyl, hydroxy$(C_1-C_6)$alkyl, or $-OCOR^{13}$, wherein $R^{13}$ is $(C_1-C_6)$alkyl, oxaalkylene according to formula (XV) or (XVI):

$-(CH_2)_aO(CR^{14}H)_b-$ (XV)

$-(CH_2)_c(O(CR^{15}H)_d)_e(CH_2)_f-$ (XVI)

wherein each $R^{14}$ and $R^{15}$ is independently H or alkyl and each a, b, c, d, e and f is independently an integer of from 1 to 20, or alkylcarbonyloxaalkylene according to formula:

$-R^{16}-C-R^{17}_3$ wherein $R^{16}$ is $(C_1-C_{12})$alkylene or $(C_1-C_{12})$oxaalkylene and each $R^{17}$ is independently H, $(C_1-C_{24})$alkyl, or $-OCOR^{18}$, wherein each $R^{18}$ is independently $(C_1-C_{24})$alkyl, provided that at least one $R^{17}$ group per radical is $-OCOR^{18}$.

6. The composition of claim 1, wherein, the fluid comprises one or more compounds that are in the liquid state at or near room temperature and about one atmosphere pressure.

7. The composition of claim 1, wherein, the fluid comprises one or more of silicone fluids and organic fluids.

* * * * *